United States Patent [19]

Matkovic et al.

[11] Patent Number: 5,175,006
[45] Date of Patent: Dec. 29, 1992

[54] METHOD OF TREATING ARTHRITIS USING GALLIUM COMPOUNDS

[75] Inventors: Velimir Matkovic, Columbus; Nicholas Gerber, Worthington, both of Ohio

[73] Assignee: The Ohio State University, Columbus, Ohio

[21] Appl. No.: 586,491

[22] Filed: Sep. 21, 1990

[51] Int. Cl.⁵ .................... A61K 31/28; A61K 33/24
[52] U.S. Cl. .................................... 424/650; 514/492
[58] Field of Search ................ 514/492; 424/604, 650

[56] References Cited

PUBLICATIONS

"Rheumatology—Prevention of Rat Adjuvant Polyarthritis by a Gallium Salt," C. R. Acad. Sc. Paris, t. 283 (Nov. 15, 1976), Delbarre et al., pp. 1469–1472.
Merck Index, 9th Ed. pp. 560–561 (1976).
Chem. Abst., vol. 105 (1986) 130055u.
Chem. Abst, vol. 111 ((1989) 170151c.

Primary Examiner—S. J. Friedman
Attorney, Agent, or Firm—W. Dennis Drehkoff

[57] ABSTRACT

Gallium compounds are utilized to treat or inhibit arthritis.

8 Claims, No Drawings

METHOD OF TREATING ARTHRITIS USING GALLIUM COMPOUNDS

FIELD OF THE INVENTION

This invention relates generally to a method of treating or inhibiting arthritis. In particular, it relates to a method of treating arthritis by the administration of gallium compounds.

BACKGROUND OF THE INVENTION

Gallium has been known for many years to be useful in the treatment of calcium bone disorders. Gallium is a metal which belongs to the Group III A Elements of the Periodic Table. The metallic compounds used, have, of course, a low order of toxicity and are pharmaceutically acceptable.

Prior U.S. Pat. Nos. 4,529,593 issued Jul. 16, 1985 to Warrell et al; 4,686,104 issued Aug. 11, 1987 to Bockman et al.; and 4,704,277 issued Nov. 3, 1987 to Bockman et al. describe methods of preventing excessive loss of calcium from human bone by the administration of pharmaceutically acceptable gallium-containing compounds. The '593 patent teaches the use of pharmaceutically acceptable gallium salts to reduce the excessive loss of bone calcium. The patent specifically teaches the use of gallium to prevent or treat disorders associated with extensive loss of calcium from bone in humans by administering to the individual a pharmaceutically acceptable gallium compound. Of special importance among the disorders which, may be thus treated are hypercalcemia, osteopenia, osteoporosis, bone destruction due to metastasis from malignant tumors and hyperparathyroidism. Gallium salts which are disclosed to be of use include nitrate, citrate, and halide, preferably the chloride, carbon, acetate, titrate, oxylate, oxide or hydrated oxide.

Loss of bone mass from increased bone resorption results in accelerated loss of calcium into the blood. This is the major cause of illness. Diseases result when significant depletion of bone calcium occurs and the structural integrity of the skeleton is compromised. The therapeutic agent of choice, according to the aforementioned patents, for treating many of the bone disorders is gallium, which both decreases bone resorption and increases bone tissue calcium content.

Heretofore, there has been no link between the treatment of bone disorders with the inhibition or treatment of arthritis, and more particularly, rheumatoid arthritis.

It has been found that gallium compounds, and gallium nitrate, in particular, are effective in treating arthritis.

The invention is directed to treating or inhibiting all types of arthritis suffered by man. However, with no intention of limiting the invention, rheumatoid arthritis is discussed.

Rheumatoid arthritis is a systemic disease of unknown cause. In the majority of patients, clinical and pathologic findings and disability are the result of chronic inflammation of synovial membranes. However, the frequency of extra-articular manifestations justifies the concept of "rheumatoid disease". Rheumatoid arthritis is one of the most crippling diseases in humans and for which there is no adequate treatment. Its symptoms include objective findings of heat, redness, swelling, tenderness, loss of motion or deformity of joints.

SUMMARY OF THE INVENTION

The present invention relates to a method of treating or inhibiting arthritis by administering to a subject in need thereof, a pharmaceutically acceptable gallium-containing compound in an amount sufficient to treat or inhibit arthritis.

DETAILED DESCRIPTION OF THE INVENTION

As indicated, the present invention relates to the use of gallium compounds in the treatment or inhibition of arthritis, particularly rheumatoid arthritis. In the past, gallium compounds have been employed to treat disorders associated with bone tissue, but have not been administered for the treatment or inhibition of arthritis.

The following experiments were designed with the administration and use of gallium compounds for the treatment and inhibition of arthritis. There are several animal models of rheumatoid arthritis widely used to test drugs for efficacy in this disease. One model is the rat adjuvant model in which an extract of *Mycobacterium butyricum* is injected into the footpad; approximately two weeks later, the animals develop swollen joints which resemble rheumatoid arthritis. The model is thoroughly described in *Immunopathology* 11:315-333 (1989).

MATERIALS AND METHODS

The study showing the utility of the present invention included thirty rats with 20 controls and 10 treated with gallium. Adjuvant induced arthritis was inducted into three groups of male rats. Group 1 was the control and received no gallium and no adjuvant induced arthritis; Group 2 received the adjuvant-induced arthritis without gallium; Group 3 received the adjuvant induced arthritis and gallium.

Chemicals

Adjuvant was prepared by homogenizing dessicated *Mycobacterium butyricum* (Baxter Scientific Products, Cincinnati, Ohio, lot # 780522, exp. March/1992, stored at 2°-8° C. in a 100 mg sealed ampoule) in Freund's incomplete adjuvant (Sigma Chemical Co., St. Louis, Mo., lot # 49F-880, stored at 0°-2° C. (light-sensitive), containing 0.85 ml of paraffin oil and 0.15 ml mannide monooleate per 1 ml solution in a 10 ml septa vial) to give a suspension of 0.75 mg *M. butyricum*/0.1 ml (made one day prior to injection). Adjuvant arthritis was produced by a single intradermal injection (using a 1 ml tuberculin syringe with a 21 gauge needle: length # 1.5") of 0.1 ml of adjuvant, on Day 0, into a footpad of the left hindpaw of male Lewis inbred rats (VAF+) (Charles River Laboratories, Inc., Portage, Mich.) weighing between 138 and 195 g (A+G+; n=10). The rats were anesthetized with ethyl ether (USP grade) inhalation before and during the adjuvant injection.

Animals

Male Lewis inbred rats (VAF+) (Charles River Laboratories, Inc. Portage, Mich.), 138 and 195 g. were housed in stainless steel cages with a bedding of hardwood chips. Animals were allowed free access to Purina Rodent Chow (Ralston Purina, St. Louis, Mo.) and tap water, maintained in a controlled environment at 21±2° C. and 50±10% relative humidity with a 12-hr light-dark cycle and acclimated for at least 1 week before use.

Adjuvant-induced arthritis (secondary lesions) occurred after a delay of approximately 15 days and was characterized by inflammation of the non-injected sites (right hindleg, forepaws and tail).

DRUG ADMINISTRATION

Gallium nitrate (Ben Venue Laboratories, Bedford, Ohio; gift from the National Cancer Institute, Bethesda, Md.) was used as received (composition: 500 mg of $Ga(NO_3)_3$ and 575 mg of trisodium citrate dihydrate in 20 ml of $H_2O$, titrated with NaOH to pH 7) and injected subcutaneously ($-1$ day from adjuvant injection) in a dose of 30 mg/kg loading dose and 10 mg/kg maintenance dose weekly, thereafter. The drug was administered one day before the adjuvant injection and continuing until the termination of the experiment (day 28). Control rats were divided in the following groups: one control group ($A+G-$; $n=8$) received the adjuvant injection without gallium nitrate injection (used a corresponding amount of trisodium citrate dihydrate solution, i.e., an identical solution as the above gallium nitrate solution from National Cancer Institute except no gallium nitrate is in solution) and the other control group ($A-G$; $n=6$) received trisodium citrate dihydrate solution but without the *M. butyricum* adjuvant injection.

Statistics

Analysis of data (Mean±standard deviation) was done using ANOVA, i.e., $A-G-$ versus $A+G-$ and $A+G-$ versus $A+B+$, where $A-$ means no arthritis; $G-$ means no gallium and "X" indicates presence of arthritis or gallium).

Results

The results on day 22 of the rotorbar @ 1 rpm times were as follows: $A-G-$ (422.33±27.33) sec, $p<n$ 0.0014); $A+G-$ (25.63±22.71 sec); and $A+G+$ (409.36±390.47 sec. $p<0.0140$). The results on day 28 of the rotorbar times were as follows: $A-G-$ (600±0 (544±177.88 sec, $p<0.001$). The rotorbar times show flexibility of the joints in the animal. The two tables below are ANOVA tests on rotorbar times.

1) Adjuvant-induced arthritis Lewis rats: time on rotorbar @ 1 rpm.

| Group | | N | MEAN | SD | SEM |
|---|---|---|---|---|---|
| A | $A-G-$ | 6 | 600 | 0 | 0 |
| B | $A+G-$ | 8 | 91.5 | 118.6 | 41.93143 |

| Source (MS) | Sum of Squares | DF | Mean Square |
|---|---|---|---|
| Between groups | 886533.4 | 1 | 886533.4 |
| Within groups | 98461.72 | 12 | 8205.144 |
| Total | 984995.1 | 13 | |

One Way Analysis of Variance (ANOVA)
F = 108.046 (MS between groups divided by MS within groups)
The p value is greater than 0.0001 (two-tailed)
The difference among the group means is extremely significant.
Number of groups = 2; total number of data points = 14
Average SD within groups = 90.58225

2) Adjuvant-induced arthritis male Lewis rats: time on rotorbar @ 1 rpm

| Group | | N | MEAN | SD | SEM |
|---|---|---|---|---|---|
| A | $A-G-$ | 6 | 422.33 | 275.33 | 112.403 |
| B | $A+G-$ | 8 | 25.625 | 22.709 | 8.028844 |

| Source (MS) | Sum of Squares | DF | Mean Square |
|---|---|---|---|
| Between groups | 539570.9 | 1 | 539570.9 |
| Within groups | 382642.9 | 12 | 31886.9 |
| Total | 922213.9 | 13 | |

One Way Analysis of Variance (ANOVA)
F = 16.92139 (MS between groups divided by MS within groups)
The p value is 0.0014 (two-tailed)
The difference among the group means is very significant.
Number of groups = 2; total number of data points = 14
Average SD within groups = 178.569

3) Adjuvant-induced arthritis male Lewis rats: time on rotorbar @ 1 rpm

| Group | | N | MEAN | SD | SEM |
|---|---|---|---|---|---|
| A | $A+G-$ | 8 | 25.625 | 22.703 | 8.028844 |
| B | $A+G+$ | 10 | 409.36 | 390.47 | 123.4775 |

| Source (MS) | Sum of Squares | DF | Mean Square |
|---|---|---|---|
| Between groups | 654455.9 | 1 | 654455.9 |
| Within groups | 1375811 | 16 | 85988.2 |
| Total | 2030267 | 17 | |

One Way Analysis of Variance (ANOVA)
F = 7.610996 (MS between groups divided by MS within groups)
The p value is 0.0140 (two-tailed)
The difference among the group means is significant.
Number of groups = 2; total number of data points = 18
Average SD within groups = 293.2375

4) Adjuvant-induced arthritis Lewis rats: Time on rotorbar @ 1 rpm

| Group | | N | MEAN | SD | SEM |
|---|---|---|---|---|---|
| A | $A+G-$ | 8 | 91.5 | 118.6 | 41.93143 |
| B | $A+G+$ | 10 | 544 | 177.0875 | 55.99998 |

| Source (MS) | Sum of Squares | DF | Mean Square |
|---|---|---|---|
| Between groups | 910027.8 | 1 | 910027.8 |
| Within groups | 380701.5 | 16 | 23793.85 |
| Total | 1290729 | 17 | |

One Way Analysis of Variance (ANOVA)
F = 38.24635 (MS between groups divided by MS within groups)
The p value is < 0.0001 (two tailed)
The difference among the group means is extremely significant.
Number of groups = 2; total number of data points = 18
Average SD within groups = 154.2525

In each test the full ANOVA table is shown, although only a few of these numbers are helpful. The numbers in the right column (MS) are equivalent to variances (SD squared). Here, the variance among the group means is significantly larger than the average variance within the groups. Thus, there are significant differences among the values of the group means. Because there are only two groups in each test, the ANOVA is identical to an unpaired two tailed t test.

Gallium containing compounds, especially gallium nitrate, in a pharmaceutically acceptable form and in dosages far below those known to be cytotoxic have been found to exert beneficial effects in treating or inhibiting arthritis.

According to the present invention, in order to obtain the beneficial effects of gallium in treating arthritis, pharmaceutically acceptable gallium containing compounds are administered to the patient in an amount sufficient to provide therapeutic levels of gallium. Therapeutic levels administered to the patient in an amount sufficient to provide therapeutic levels of gallium. Therapeutic levels are obtained when gallium is present in a steady state concentration in blood. Typically, the amount of gallium nitrate administered to achieve a steady state concentration in blood is from about 0.5 to about 4 mg/per kg of body weight. Preferably, this amount ranges from about 0.5 to about 2.5 mg/per kg of body weight.

Gallium containing compounds, effective with this invention, may be any gallium containing compounds in non-nephrotoxic amounts to inhibit or treat arthritis in patients suffering from arthritis by administering to a patient a therapeutically effective amount of such a compound. The compounds may be selected from the group consisting of gallium nitrate, gallium citrate, gallium chloride, gallium carbonate, gallium acetate, gallium tartrate, gallium oxylate, gallium oxide and hydrated gallium oxide.

Gallium containing compounds are useful in formulations having a variety of routes of administration. The route(s) of administration useful in a particular application for the inhibition or treatment of arthritis is apparent to one skilled in the art. Routes of administration include but not limited to topical, transdermal, parenteral, gastrointestinal, transbronchial and transalveolar.

Formulations of gallium containing compounds suitable for topical application include, but are not limited to, implants, ointments, creams, resins and gels. Formulations suitable for transdermal application include, but are not limited to, suspensions, oils, creams and ointments applied directly or attached to a protective carrier such as a patch. Formulations suitable for parenteral administration include, but are not limited to, sterile solutions for intravenous, intramuscular or subcutaneous injection. Formulations suitable for gastrointestinal administration include, but are not limited to, pills or liquids for ingesting and suppositories for rectal administration. Formulations suitable for transbronchial and transalveolar administration include, but are not limited to, various types of aerosols for inhalation. The above-mentioned formulations are meant to describe but not limit the methods of administering gallium containing compounds. The methods of making the various formulations are within the ability of one skilled in the art and need not be described in detail.

The terms and expressions which had been employed are used as terms of description and not of limitation, and there is no intention in the use of such terms and expressions of excluding any equivalents of the feature shown and described or portions thereof, it being recognized that various modifications are possible within the scope of the invention.

What is claimed is:

1. A method of treating rheumatoid arthritis in humans comprising administering an effective amount of pharmaceutically acceptable gallium nitrate suitable to provide therapeutic levels of gallium to a patient in need thereof.

2. A method according to claim 1 wherein the gallium is administered via a route selected from the group consisting of topical, transdermal, parenteral, gastrointestinal, transbronchial and transalveolar.

3. The method according to claim 1 wherein the gallium nitrate is administered in an amount sufficient to maintain steady state blood concentrations.

4. The method according to claim 1 wherein the amount of gallium administered is about 0.5 to about 4.0 mg/kg of body weight.

5. A method of treating rheumatoid arthritis in humans comprising administering an effective amount of pharmaceutically acceptable gallium containing compound selected from the group consisting of gallium nitrate, gallium citrate, gallium phosphate, gallium chloride, gallium fluoride, gallium carbonate, gallium acetate, gallium tartrate, gallium maltol, gallium oxylate, gallium formate, gallium oxide and hydrated gallium oxide.

6. The method according to claim 5 wherein the gallium-containing compound is administered a route selected from the group consisting of topical, transdermal, parenteral, gastrointestinal, transbronchial, and transalveolar.

7. The method according to claim 5 wherein the gallium containing compound is administered in an amount sufficient to maintain steady state blood concentrations.

8. The method according to claim 5 wherein the amount of the gallium administered is about 0.5 to about 4.0 mg/kg of body weight.

* * * * *